United States Patent [19]

Leckie

[11] 4,172,453

[45] Oct. 30, 1979

[54] BELT-TYPE RESTRAINT DEVICE

[75] Inventor: George B. Leckie, Ottawa, Canada

[73] Assignee: Irvin Industries Canada Ltd., Fort Erie, Canada

[21] Appl. No.: 847,754

[22] Filed: Nov. 2, 1977

[51] Int. Cl.² ............................................. A61F 13/00
[52] U.S. Cl. .................................................. 128/133
[58] Field of Search ................................ 128/132–135, 128/94; 70/16, 18

[56] References Cited

U.S. PATENT DOCUMENTS

| | | | |
|---|---|---|---|
| 2,425,489 | 8/1947 | Peterson | 128/134 |
| 2,449,882 | 9/1948 | Daniels | 128/133 |
| 3,324,851 | 6/1967 | Posner | 128/134 |
| 3,474,781 | 10/1969 | Gaylord | 128/134 |
| 3,812,852 | 5/1974 | Konvalin | 128/134 |
| 3,923,050 | 12/1975 | Zeide et al. | 128/94 |

FOREIGN PATENT DOCUMENTS 1350503  12/1963  France .................................... 128/134

Primary Examiner—Lawrence W. Trapp
Attorney, Agent, or Firm—McAulay, Fields, Fisher & Goldstein

[57] ABSTRACT

A belt-type restraint device, for restraining a person, has a belt for forming a girdle about the waist of the person and restraint means for securing the wrists of the person to the front of the belt. The restraint means are formed of loops continuous with the webbing of the belt to allow a single latching buckle at the back of the belt to simultaneously adjust and lock both the belt and the loops.

10 Claims, 4 Drawing Figures

BELT-TYPE RESTRAINT DEVICE

BACKGROUND OF THE INVENTION

This invention relates in general to belt-type restraint devices for restraining a person by securing the wrists to a belt locked about the waist.

The advantages of the belt-type restraint devices, of which the present invention is intended as an improvement, are well known and include the fact that once properly secured, it is difficult to break loose or to do much damage while secured.

However, there are a number of disadvantages inherent in the belt-type restraint devices presently in widespread use. In general these devices are quite bulky and heavy. They require a lock to secure the girdling belt about the waist of the person and an individual lock for each shackle which secures the wrists to the belt. Additionally, the shackles are normally made of metal thereby adding to the bulk and weight of the restraint device. The prior art devices are therefore not only a bother to carry when not in use, but also are highly visible when in use. High visibility tends to result in "public relations" problems when a prior art restraint belt is utilized during the transportation of restrained persons by public transportation.

Accordingly, it is a major object of this invention to provide a belt-type restraint device which is lighter in weight and less bulky then are previously known devices and which is therefore easier to carry and simpler to use.

It is a further and related purpose of this invention to eliminate the metal shackles in order to achieve the above objectives.

It is a further purpose of this invention to provide this type of device which, in use, will attain the required restraing but which will make it feasible to restrain an individual who is then transported in public conveyances and in public places with minimum visibility as to the fact of the restraint.

It is also a purpose of this invention to achieve all of the above results in a device which is fully as secure as any previously known devices. Indeed, handcuffs, and to some extent metal shackles, permit a certain degree of mobility for the hands which at times allows the restrained individual to defeat and even break the devices. Accordingly, it is a purpose of this invention to reduce such mobility and thus enhance the security of the restraint device.

It is important that the restraint device be simple to use and that it be coupled to the individual being restrained by means of a single latching action. Accordingly, it is another purpose of this invention to provide a single latch restraint device.

BRIEF DESCRIPTION

In brief, the embodiment of the invention disclosed herein restrains a person by securing the person's wrists in loops of a fabric belt girdling the waist of the individual. The belt buckle is in the back, not in the front. The wrists of the individual are secured by two loops formed as a continuous part of the belt. This continuous construction results in a device wherein the tightening of the belt around the person's waist and the tightening of the wrist restraining loops occur simultaneously. The belt webbing is threaded through two separate metal grips at the front of the belt to form two separate wrist restraining loops. The two loops are spaced from one another by a non-adjustable portion of the belt extending between the two metal grips. The circumference of the belt is adjustable by means of passing the belt around a friction bar associated with the clip that latches into the buckle at the back of the belt. The wrist loops are threaded around cross bars at the two spaced apart metal grips and are adjustable. Tightening the belt around the waist of the person being restrained pulls the belt web through the metal grips thereby also tightening the wrist loops.

DESCRIPTION OF THE PREFERRED EMBODIMENTS

Figure 1:
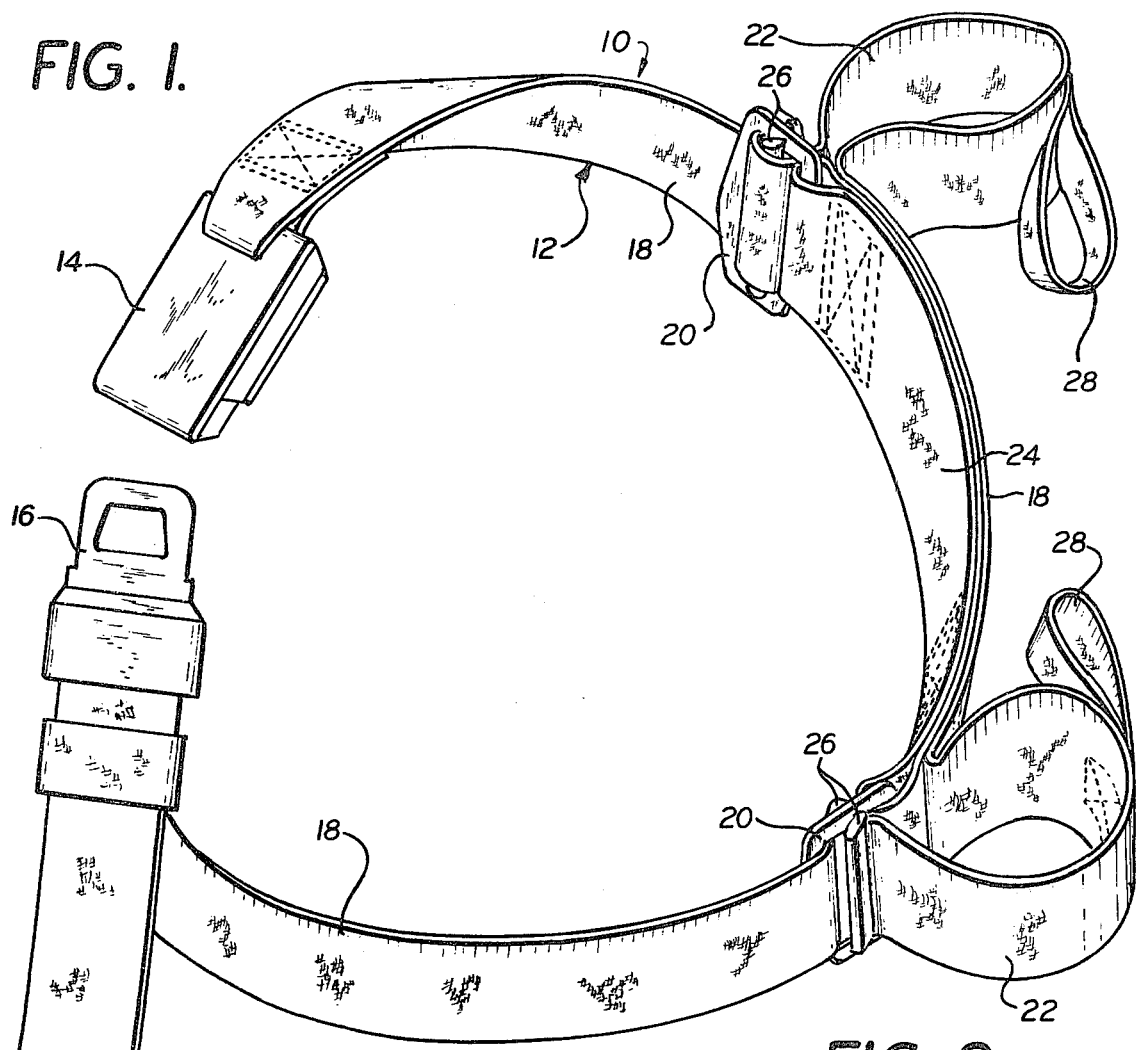
FIG. 1 is a perspective view of a belt-type restraint device according to the present invention.
Figure 2:
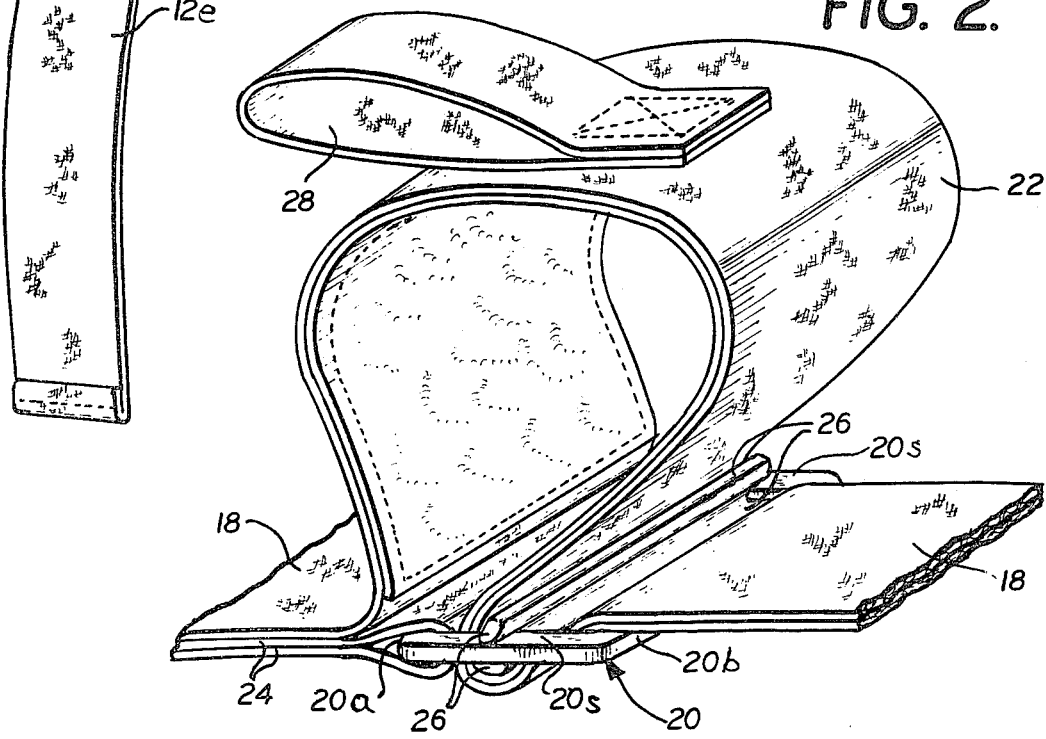
FIG. 2 is an enlarged partial view in perspective of the device of FIG. 1, showing a wrist restraining loop and associated adjustment buckle in detail.
Figure 3:
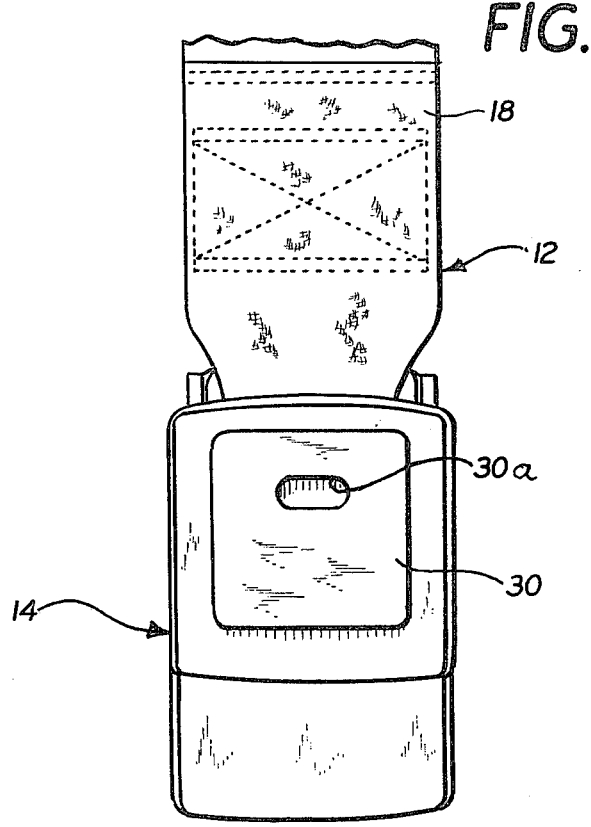
FIG. 3 is a view of the latch actuating surface of the latching buckle for the belt.
Figure 4:
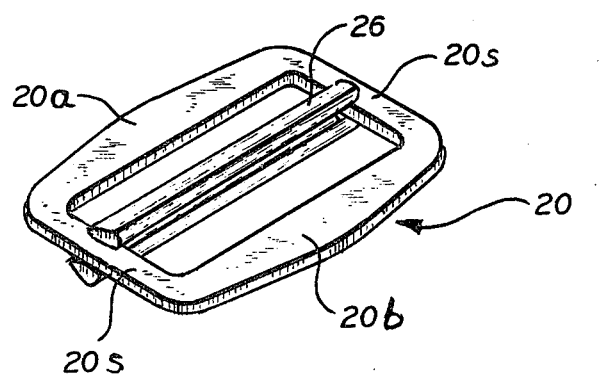
FIG. 4 is a perspective view of the adjustment buckle used to form the loop of FIG. 2 with the belt webbing removed to reveal the grip structure.

The FIGS. all refer to the same embodiment. As shown therein, the belt-type restraint device 10 of this invention includes a belt portion 12 having a buckle 14 and clip 16 so as to fasten the belt on an individual. The webbing 18 of the belt portion 12 is threaded through a friction bar (not shown) in the clip 16 so that the circumference of the belt portion 12 can be adjusted and the restraint device 10 thereby tightly drawn around the waist of the person being restrained.

The webbing 18 is threaded through two spaced apart metal grips 20 to form two spaced apart loops 22. These loops 22 are employed to tightly fasten the wrists of the individual being restrained to the belt at the position of the grips 20. The restraint device 10 includes a strap portion 24, which is made of the same type of webbing as the rest of the belt, but which is connected between the two grips 20 and which thereby fixes the distance apart of the two grips 20 and thus of the two loops 22. This fixed length strap portion 24 is overlayed by belt webbing 18 that is threaded through the grips 20. This overlayed portion of the belt 12 and the strap portion 24 are sewn together so that tension forces in the belt extend continuously through the webbing 18 that constitutes the belt portion 12, loop portion 22 and strap portion 24 of this restraint device.

The grips 20 are rectangular metal pieces, each having an inboard end bar 20a, an outboard end bar 20b, side bars 20s and a cross bar 26. The cross bar 26 is V-shaped in cross section and is positioned across the two side bars 20s so that the cross bar 26 is free to move along the side bars 20s. Thus the side bars 20s operate as rails along which the cross bar 26 can move.

The ends of the strap portion 24 are looped around the inboard ends 20a of the grips and sewn in place. The belt portion 12 is passed over the outboard end 20b of each grip, under and around the cross bar 26 and then along the front facing surface of the strip 24 where the belt webbing 18 and strap 24 webbing are sewn together. Tabs 28 in the form of loops are sewn to the belt portion of the webbing 18 at positions where the loops 22 are formed. These tabs aid the peace officer or the like to pull the restrained individual's wrists into position and also aid in releasing the wrists once the buckle has been opened.

The metal grip 20 is the same as a type of adjustment buckle frequently used on a parachute. It prevents a restrained person from opening the loops 22 by thrusting his wrists in an outboard direction. Thus, thrusting the wrists outboard will cause the webbing 18 to pull the movable cross bar 26 outboard thereby gripping the webbing between the outboard end bar 20b. It is for this reason that the jaw of the cross bar 26 faces the outboard end bar 20b. Yet once the buckle 14 in the back has been released, the wrist loops 22 can be opened by pulling the tabs 28 in an inboard direction (that is, toward each other). When this is done, the cross bar 26 moves inboard enough so that the webbing 18 can slide over the end bar 20b and around the cross bar 26 to open the loop 22.

The buckle 14 and clip 16 arrangement may be similar to that shown in U.S. Pat. No. 4,052,775 issued Oct. 11, 1977. However, in order to enhance security, the top of the buckle 14 is covered by a plastic face plate 30 having a small opening 30a so that the only access to the release lever is by way of a prod or key that is inserted through the opening 30a and pressed inward to depress the lever and release the clip. This prevents finger or thumb release of the buckle. Further, in order to enhance security, the top of the buckle 14, where access to the release lever is available, is turned inward against the body of the person being restrained rather than, as is usual, turned outward. Thus, to release the restraint device 10 one not only has to have a key available that will fit through the opening 30a but one also has to turn the buckle 14 and clip 16 around so as to have access to the opening 30a.

In operation, the arresting officer pulls the loops 22 open so that the hands of the person being restrained can be passed through the loops 22. The arms of the restrained person are preferably crossed so that his left wrist is held by the right loop 22 and vice versa. Loops 22 are then pulled reasonably tight and the belt portion 12 is drawn around the waist of the person being restrained. The end 12e of the belt is drawn through the clip 16 until the belt is as tight as desired around the person being restrained. The clip 16 and buckle 14 are fastened and the belt can continue to be drawn as tight as desired. The drawing of the belt tighter, sets up tension in the webbing 18 which is transmitted through the webbing to the loop portions 22 thereby pulling the loop portions 22 tight around the wrists of the person being restrained at the same time as the belt 12 is being pulled tight around the waist of the person. Wrist movement within the loops 22 by the person being restrained causes the cross bar 26 to jam against one end of the grip 20 thereby preventing the loops 22 from opening under pressure from forces generated within the loops 22.

Although a presently preferred embodiment of the invention has been described, there are certain variations that could be made without departing from the scope of this invention. For example, the adjustment buckle or grip 20 has been referred to as a grip because of the manner in which the movable cross bar 26 will serve to grip the webbing 18 when a restrained individual attempts to move his wrists in a outboard direction. However, depending on the precise function to be achieved and the trade-off between security and ease of use, the grip 18 might be replaced by any one of a number of types of adjustment buckles which permit and even facilitate movement of the webbing 18 therethrough under tension so that the wrist loops 22 can be tightened around the wrists of the restrained individual at the same time that the girdle portion of the belt 12 is tightened around the waist of the individual.

What is claimed is:

1. A belt-type restraint device for releasably securing the wrists of a person to a girdle formed about the waist of the person, comprising:
   a flexible belt member,
   latching means to adjust the size of said flexible belt member and to latch it, under tension, about the waist of the person,
   first and second spaced apart slip loop forming means, each operable to releasably form a loop in said flexible belt,
   an elongated spacing strap having first and second ends secured respectively to said first and second loop forming means to restrain said loop forming means from separating by more than a predetermined distance.

2. The device of claim 1 further comprising:
   first and second wrist restraining loops, one each at said first and second slip loop forming means respectively, each of said loops being formed of and continuous with said flexible belt member, any increase or decrease in the length of any one of said loops being matched by an equal decrease or increase, respectively, in the length of the rest of said flexible member that is around the waist of the person on whom it is buckled.

3. The restraint device of claim 2 further comprising:
   uni-directional gripping means at each of said slip loop forming means to transmit tension in said flexible belt member to said wrist restraining loops to tighten said loops in response to said tension and to prevent tension developed in said loops from being transmitted to the rest of said flexible belt member to prevent opening of said loops in response to tension induced on said loops.

4. The restraint device of claim 2 wherein said slip loop forming means are spaced from said latching means sufficiently so that said restraining loops are in the front portion of said belt member when said latching means are coupled at the back of the person being restrained.

5. The restraint device of claim 3 wherein said slip loop forming means are spaced from said latching means sufficiently so that said restraining loops are in the front portion of said belt member when said latching means are coupled at the back of the person being restrained.

6. A belt-type restraint device for releasably securing at least one wrist of a person to a girdle formed about the waist of the person, comprising:
   a flexible belt member,
   latching means to adjust the size of said flexible belt member and to latch it, under tension, about the waist of the person,
   a first adjustment buckle fixed to said flexible belt member at a first predetermined position on said belt member, and
   a first wrist restraining loop at said first adjustment buckle, said first loop formed of and continuous with said flexible belt member, any increase or decrease in the length of said first loop being matched by an equal decrease or increase, respectively, in the length of the rest of said flexible member that is around the waist of the person on whom it is buckled.

7. The restraint device of claim 6 further comprising:
a second adjustment buckle fixed to said flexible belt member at a second predetermined position on said belt member, and
a second wrist restraining loop at said second adjustment buckle, said second loop being formed of and continuous with said flexible belt member, any increase or decrease in length of said second loop being matched by an equal decrease or increase, respectively, in the length of the rest of said flexible member that is around the waist of the person on whom it is buckled.

8. The restraint device of claim 7 further comprising:
a spacing strap between said first and second adjustment buckles to prevent said adjustment buckles and said restraining loops from separating by more than a predetermined distance.

9. The restraint device of claim 8 wherein said first and second restraining loops are spaced from said latching means sufficiently so that said restraining loops are in the front portion of said belt member when said latching means are coupled at the back of the person being restrained.

10. The restraint device of claim 7 wherein said first and second restraining loops are spaced from said latching means sufficiently so that said restraining loops are in the front portion of said belt member when said latching means are coupled at the back of the person being restrained.

* * * * *